US012682989B2

(12) United States Patent
Yoon et al.

(10) Patent No.: US 12,682,989 B2
(45) Date of Patent: Jul. 14, 2026

(54) ELECTRONIC APPARATUS AND CONTROL METHOD THEREOF

(71) Applicant: SAMSUNG ELECTRONICS CO., LTD., Suwon-si (KR)

(72) Inventors: Sanghyuk Yoon, Suwon-si (KR); Heejun Song, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 861 days.

(21) Appl. No.: 18/076,625

(22) Filed: Dec. 7, 2022

(65) Prior Publication Data

US 2023/0197211 A1 Jun. 22, 2023

Related U.S. Application Data

(63) Continuation of application No. PCT/KR2022/011941, filed on Aug. 10, 2022.

(30) Foreign Application Priority Data

Dec. 20, 2021 (KR) ........................ 10-2021-0183173

(51) Int. Cl.
*G16H 10/20* (2018.01)
*G16H 50/70* (2018.01)

(52) U.S. Cl.
CPC .............. *G16H 10/20* (2018.01); *G16H 50/70* (2018.01)

(58) Field of Classification Search
CPC ........ G16H 10/20; G16H 50/70; G16H 40/67; G16H 50/20

(Continued)

(56) References Cited

U.S. PATENT DOCUMENTS 9,400,956 B2 * 7/2016 Eggebraaten ............ G06N 7/01
2014/0280144 A1 * 9/2014 Heit ...................... G06F 16/285
707/737

(Continued)

FOREIGN PATENT DOCUMENTS

CN 110990546 A 4/2020
CN 111177307 A 5/2020

(Continued)

OTHER PUBLICATIONS

Communication dated Dec. 6, 2022, issued by the International Searching Authority in counterpart International Application No. PCT/KR2022/011941 (PCT/ISA/210).

(Continued)

*Primary Examiner* — Angelica Ruiz
(74) *Attorney, Agent, or Firm* — Sughrue Mion, PLLC

(57) ABSTRACT

An electronic apparatus includes a memory, and a processor connected to the memory and configured to control the electronic apparatus, where the processor is configured to identify a plurality of counseling end histories among a plurality of counseling histories stored in the memory, each of the plurality of counselling end histories indicating that a counselling has failed to answer a user query, based on a ratio of the plurality of counseling end histories to the plurality of counseling histories being equal to or greater than a threshold ratio, identify a first user query based on the plurality of counseling end histories, and based on a number of second user queries having a similarity to the identified first user query being equal to or greater than a first threshold number, acquire an answer to the first user query.

16 Claims, 11 Drawing Sheets

(58) Field of Classification Search
USPC ............................................................ 705/2
See application file for complete search history.

(56) References Cited

U.S. PATENT DOCUMENTS

| | | | |
|---|---|---|---|
| 2018/0032881 A1 | 2/2018 | Hosn et al. | |
| 2019/0042988 A1* | 2/2019 | Brown | ................ G06F 16/9535 |
| 2019/0095428 A1 | 3/2019 | Asano et al. | |
| 2019/0370283 A1* | 12/2019 | Church | .................... G06N 3/08 |
| 2021/0034680 A1* | 2/2021 | Ozaki | ................ G06F 16/9017 |
| 2021/0357378 A1* | 11/2021 | Urdiales | ............. G06F 16/2237 |

FOREIGN PATENT DOCUMENTS

| | | | |
|---|---|---|---|
| JP | 2014167722 A | 9/2014 | |
| JP | 202071690 A | 5/2020 | |
| KR | 10-2018-0017342 A | 2/2018 | |
| KR | 101883185 B1 | 7/2018 | |
| KR | 10-2019-0059731 A | 5/2019 | |
| KR | 1020190066988 A | 6/2019 | |
| KR | 10-1996557 B1 | 7/2019 | |
| KR | 10-2019-0097947 A | 8/2019 | |
| KR | 10-2047385 B1 | 11/2019 | |
| KR | 10-2020-0013843 A | 2/2020 | |
| KR | 10-2020-0032893 A | 3/2020 | |
| KR | 102096450 * | 5/2020 | ............. G06Q 30/02 |

OTHER PUBLICATIONS

Communication dated Dec. 6, 2022, issued by the International Searching Authority in counterpart International Application No. PCT/KR2022/011941 (PCT/ISA/237).
Communication dated Mar. 18, 2026, issued by the Korean Ministry of Intellectual Property Administration in Korean Application No. 10-2021-0183173.

* cited by examiner

Figure 2:
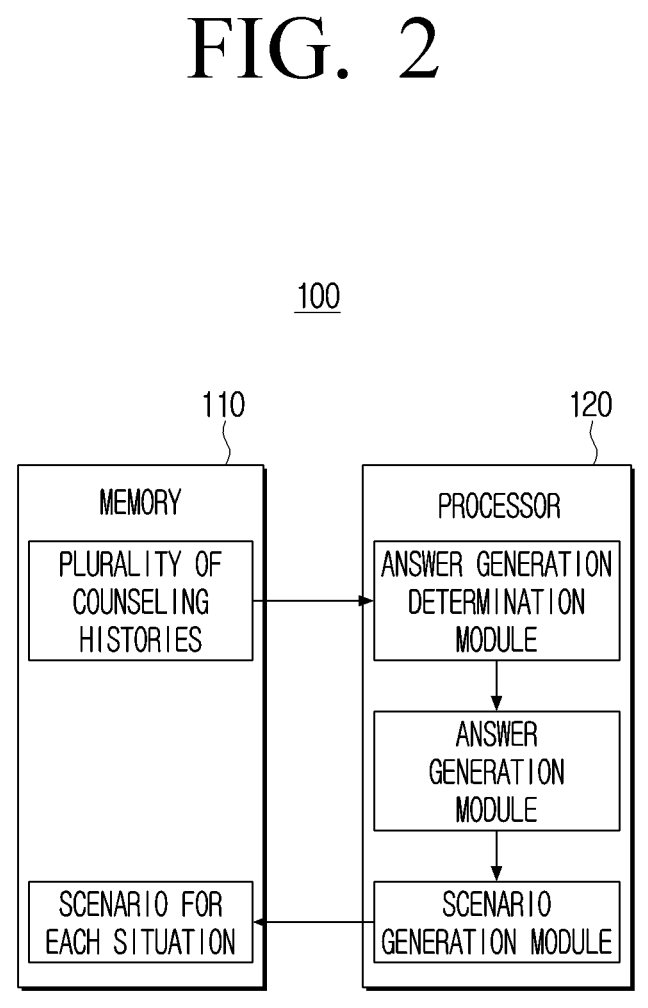

| MEMORY | PROCESSOR |
|---|---|
| PLURALITY OF COUNSELING HISTORIES | ANSWER GENERATION DETERMINATION MODULE |
| | ANSWER GENERATION MODULE |
| SCENARIO FOR EACH SITUATION | SCENARIO GENERATION MODULE |

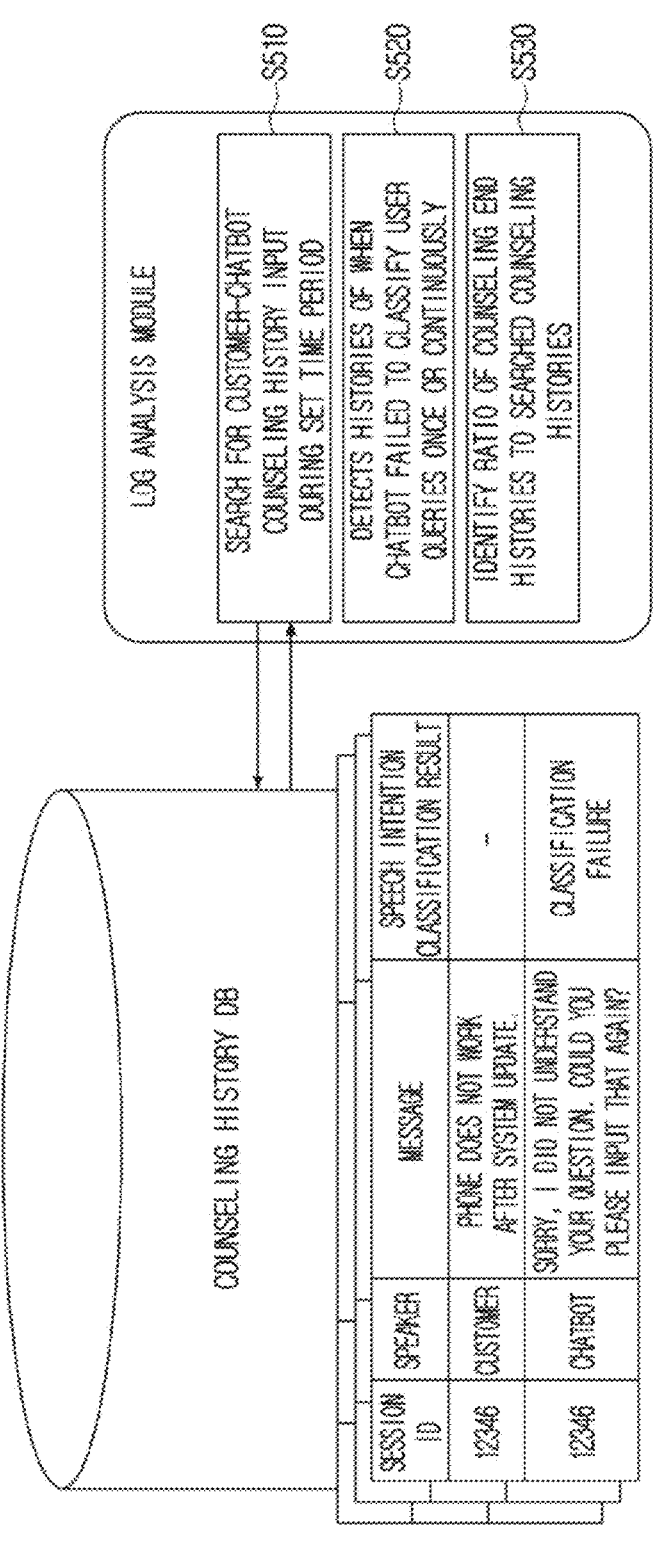

LOG ANALYSIS MODULE

| | |
|---|---|
| SEARCH FOR CUSTOMER-CHATBOT COUNSELING HISTORY INPUT DURING SET TIME PERIOD | S510 |
| DETECTS HISTORIES OF WHEN CHATBOT FAILED TO CLASSIFY USER QUERIES ONCE OR CONTINUOUSLY | S520 |
| IDENTIFY RATIO OF COUNSELING END HISTORIES TO SEARCHED COUNSELING HISTORIES | S530 |

COUNSELING HISTORY DB

| SESSION ID | SPEAKER | MESSAGE | SPEECH INTENTION CLASSIFICATION RESULT |
|---|---|---|---|
| 12346 | CUSTOMER | PHONE DOES NOT WORK AFTER SYSTEM UPDATE. | - |
| 12346 | CHATBOT | SORRY, I DID NOT UNDERSTAND YOUR QUESTION. COULD YOU PLEASE INPUT THAT AGAIN? | CLASSIFICATION FAILURE |

FIG. 6

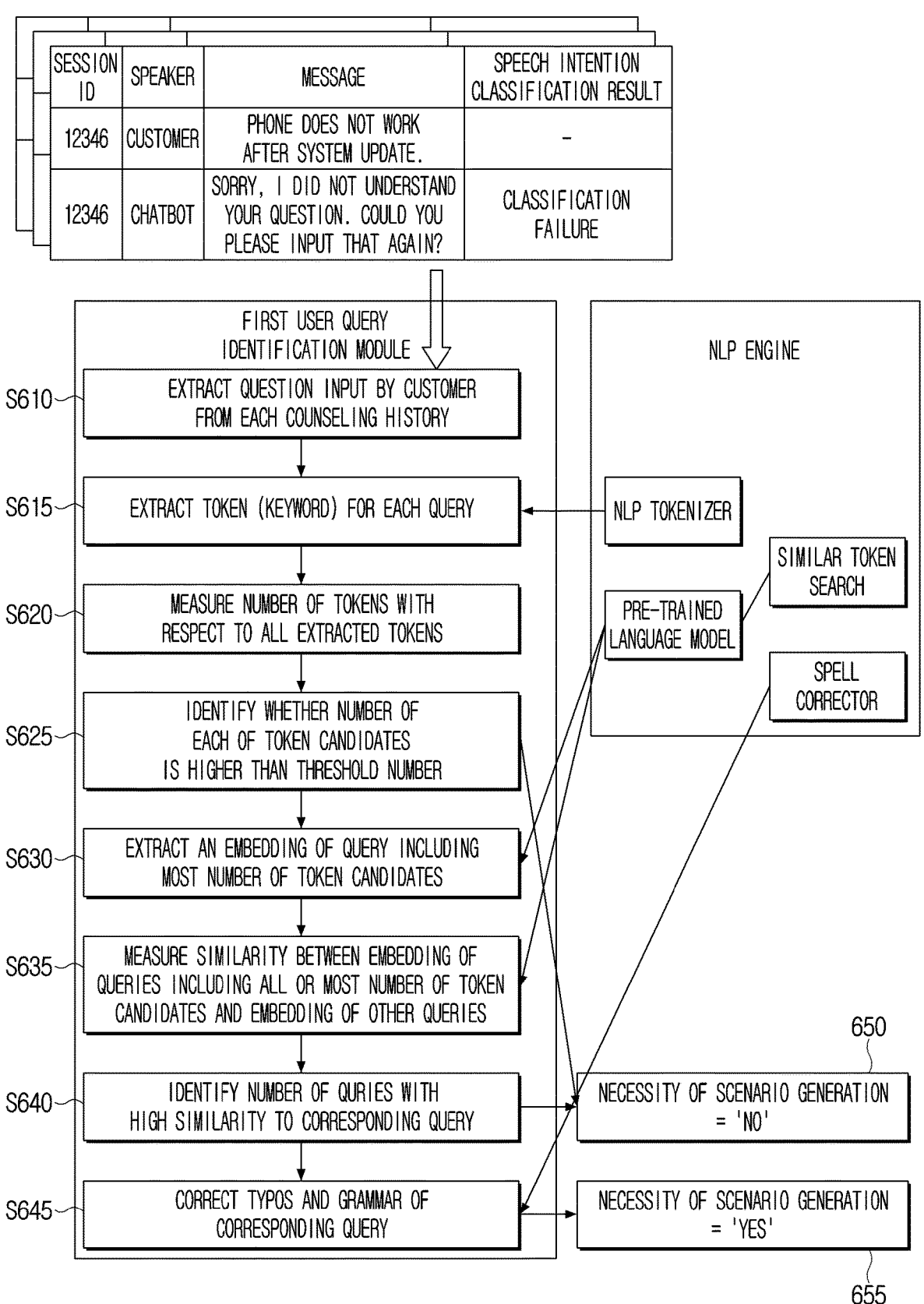

| SESSION ID | SPEAKER | MESSAGE | SPEECH INTENTION CLASSIFICATION RESULT |
|---|---|---|---|
| 12346 | CUSTOMER | PHONE DOES NOT WORK AFTER SYSTEM UPDATE. | - |
| 12346 | CHATBOT | SORRY, I DID NOT UNDERSTAND YOUR QUESTION. COULD YOU PLEASE INPUT THAT AGAIN? | CLASSIFICATION FAILURE |

FIRST USER QUERY IDENTIFICATION MODULE

NLP ENGINE

S610 — EXTRACT QUESTION INPUT BY CUSTOMER FROM EACH COUNSELING HISTORY

S615 — EXTRACT TOKEN (KEYWORD) FOR EACH QUERY

NLP TOKENIZER

S620 — MEASURE NUMBER OF TOKENS WITH RESPECT TO ALL EXTRACTED TOKENS

SIMILAR TOKEN SEARCH

S625 — IDENTIFY WHETHER NUMBER OF EACH OF TOKEN CANDIDATES IS HIGHER THAN THRESHOLD NUMBER

PRE-TRAINED LANGUAGE MODEL

SPELL CORRECTOR

S630 — EXTRACT AN EMBEDDING OF QUERY INCLUDING MOST NUMBER OF TOKEN CANDIDATES

S635 — MEASURE SIMILARITY BETWEEN EMBEDDING OF QUERIES INCLUDING ALL OR MOST NUMBER OF TOKEN CANDIDATES AND EMBEDDING OF OTHER QUERIES

S640 — IDENTIFY NUMBER OF QURIES WITH HIGH SIMILARITY TO CORRESPONDING QUERY

650

NECESSITY OF SCENARIO GENERATION = 'NO'

S645 — CORRECT TYPOS AND GRAMMAR OF CORRESPONDING QUERY

NECESSITY OF SCENARIO GENERATION = 'YES'

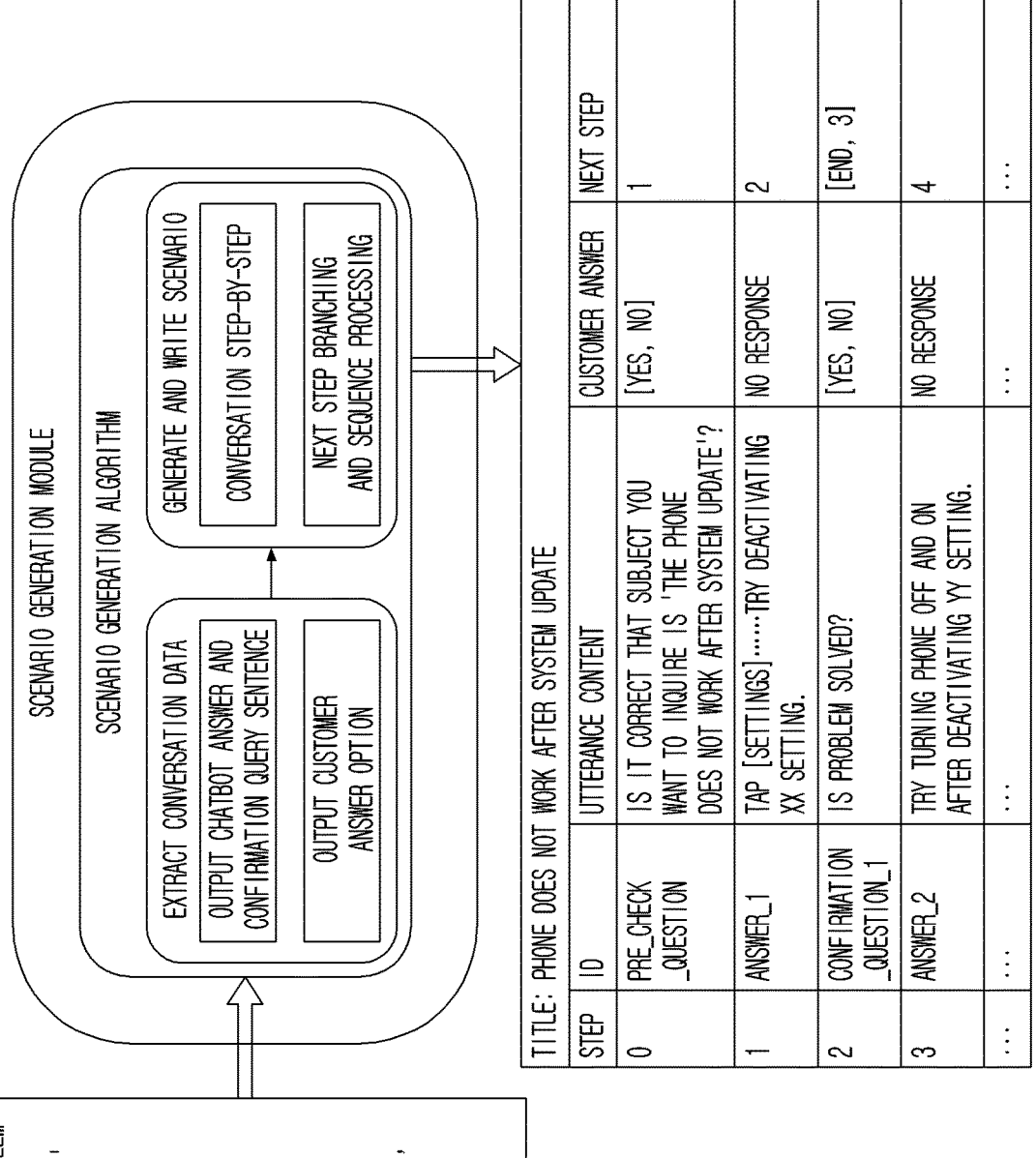

CONVERSATION TYPE: 'SOLVING PROBLEM'

SEARCH SOURCE: 'COUNSELOR MANUAL'

TITLE: PHONE DOES NOT WORK AFTER SYSTEM UPDATE.

OUTPUT: [
['TAP [SETTINGS]……TRY DEACTIVATING XX SETTING.'],
['TRY TURNING PHONE OFF AND ON AFTER DEACTIVATING YY SETTING.'],
… …
]

SCENARIO GENERATION MODULE

SCENARIO GENERATION ALGORITHM

EXTRACT CONVERSATION DATA

OUTPUT CHATBOT ANSWER AND CONFIRMATION QUERY SENTENCE

OUTPUT CUSTOMER ANSWER OPTION

GENERATE AND WRITE SCENARIO

CONVERSATION STEP-BY-STEP

NEXT STEP BRANCHING AND SEQUENCE PROCESSING

TITLE: PHONE DOES NOT WORK AFTER SYSTEM UPDATE

| STEP | ID | UTTERANCE CONTENT | CUSTOMER ANSWER | NEXT STEP |
|---|---|---|---|---|
| 0 | PRE_CHECK _QUESTION | IS IT CORRECT THAT SUBJECT YOU WANT TO INQUIRE IS 'THE PHONE DOES NOT WORK AFTER SYSTEM UPDATE'? | [YES, NO] | 1 |
| 1 | ANSWER_1 | TAP [SETTINGS]……TRY DEACTIVATING XX SETTING. | NO RESPONSE | 2 |
| 2 | CONFIRMATION _QUESTION_1 | IS PROBLEM SOLVED? | [YES, NO] | [END, 3] |
| 3 | ANSWER_2 | TRY TURNING PHONE OFF AND ON AFTER DEACTIVATING YY SETTING. | NO RESPONSE | 4 |
| … | … | … | … | … |

FIG. 10

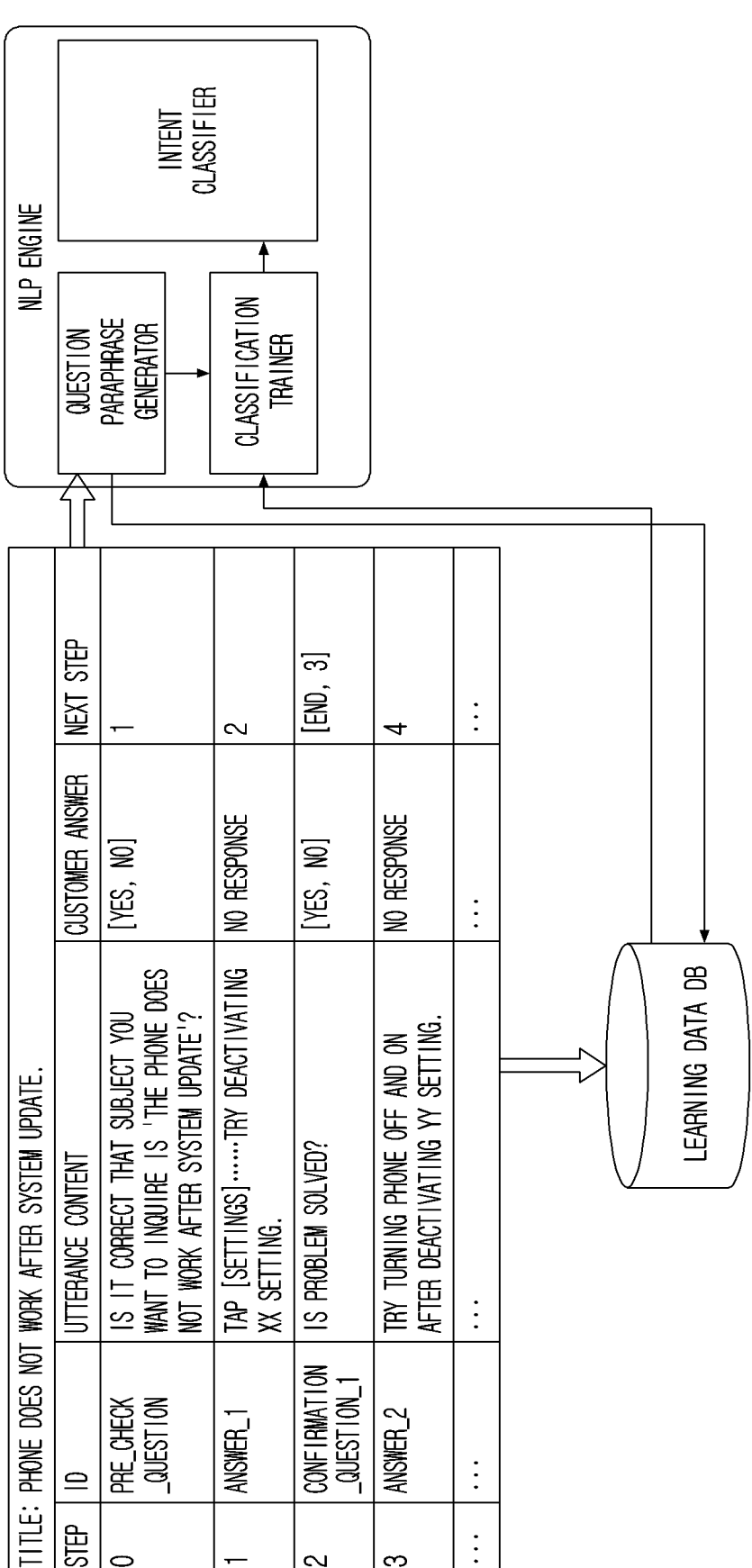

TITLE: PHONE DOES NOT WORK AFTER SYSTEM UPDATE.

| STEP | ID | UTTERANCE CONTENT | CUSTOMER ANSWER | NEXT STEP |
|---|---|---|---|---|
| 0 | PRE_CHECK _QUESTION | IS IT CORRECT THAT SUBJECT YOU WANT TO INQUIRE IS 'THE PHONE DOES NOT WORK AFTER SYSTEM UPDATE'? | [YES, NO] | 1 |
| 1 | ANSWER_1 | TAP [SETTINGS]······TRY DEACTIVATING XX SETTING. | NO RESPONSE | 2 |
| 2 | CONFIRMATION _QUESTION_1 | IS PROBLEM SOLVED? | [YES, NO] | [END, 3] |
| 3 | ANSWER_2 | TRY TURNING PHONE OFF AND ON AFTER DEACTIVATING YY SETTING. | NO RESPONSE | 4 |
| ... | ... | ... | ... | ... |

NLP ENGINE

QUESTION PARAPHRASE GENERATOR

CLASSIFICATION TRAINER

INTENT CLASSIFIER

LEARNING DATA DB

ELECTRONIC APPARATUS AND CONTROL METHOD THEREOF

CROSS-REFERENCE TO RELATED APPLICATION(S)

This application is a bypass continuation of International Application No. PCT/KR2022/011941, filed on Aug. 10, 2022, which is based on and claims priority to Korean Patent Application No. 10-2021-0183173, filed on Dec. 20, 2021, in the Korean Intellectual Property Office, the disclosures of which are incorporated by reference herein in their entireties.

BACKGROUND

Field

The disclosure relates to an electronic apparatus and a control method thereof. More particularly, the disclosure relates to an electronic apparatus providing a conversation function with a user and a control method thereof.

Description of the Prior Art

With the development of electronic technology, various types of electronic apparatuses have been developed. Particularly, electronic apparatuses such as a voice assistant or a chatbot that provides a conversation function with a customer through text or voice have been developed recently.

A voice assistant mainly aims to execute commands for customer products in an open domain whereas a chatbot mainly aims to process customer inquiries and conduct counseling for a specific domain. Accordingly, the voice assistant needs to improve an ability of executing commands of various domains for improving performance whereas the chatbot needs to increase domain conversation topics and conversation data with customers who have problems in a specific domain.

However, there is a problem that the chatbot cannot provide answers to all inquiries. For example, the chatbot can answer a user query only after an answer is manually generated by an administrator. In other words, when an answer is not stored in the chatbot, for example, when a question about a new problem occurring in a new product is received, the chatbot cannot solve the problem until the administrator creates and stores the answer.

Thus, it is necessary to develop a method that can increase customer satisfaction while reducing the manual operation of the administrator.

SUMMARY

The disclosure has been made in accordance with the problem described above, and the disclosure is to provide an electronic apparatus for generating an answer scenario for a conversation function with a user and a control method thereof.

According to an embodiment of the disclosure, an electronic apparatus includes a memory, and a processor connected to the memory and configured to control the electronic apparatus, where the processor is configured to identify a plurality of counseling end histories among a plurality of counseling histories stored in the memory, each of the plurality of counseling end histories indicating that a counseling has failed to answer a user query, based on a ratio of the plurality of counseling end histories to the plurality of counseling histories being equal to or greater than a threshold ratio, identify a first user query based on the plurality of counseling end histories, and based on a number of second user queries having a similarity to the identified first user query being equal to or greater than a first threshold number, acquire an answer to the first user query.

The processor may be further configured to acquire a dialogue-type scenario with respect to the first user query based on the acquired answer, and store the acquired scenario in the memory.

The processor may be further configured to, based on a counseling including a query having a similarity to the first user query equal to or greater than a threshold value being started, perform a counseling based on the acquired scenario.

The processor may be further configured to identify a plurality of counseling histories for a predetermined previous time period among the plurality of counseling histories and a plurality of counseling end histories for the predetermined previous time period, and identify whether a ratio of the plurality of counseling end histories identified for the predetermined previous time period to the plurality of counseling histories identified for the predetermined previous time period are equal to or greater than the threshold ratio.

The processor may be configured to identify a plurality of keywords in user queries included in the plurality of counseling end histories, identify a predetermined number of keywords based on a number of each of the plurality of keywords, and based on the number of each of the identified keywords being equal to or greater than a second threshold number, identify, as the first user query, a user query included in a history including the most identified keywords among the plurality of counseling end histories.

The processor may be further configured to acquire the answer by searching for a keyword included in the first user query in at least one of a counseling manual, the plurality of counseling histories, and an external search engine.

The processor may be further configured to, based on the keyword included in the first user query being not searched in the counseling manual, additionally identify a keyword in a counseling end history including the first user query, and acquire the answer by searching for the additionally identified keyword in the counseling manual.

The processor may be further configured to, based on counseling histories including the keyword included in the first user query being searched among the plurality of counseling histories, acquire the answer based on a relatively short counseling history among the searched counseling histories.

The processor may be further configured to acquire the answer by searching for the keyword included in the first user query in the counseling manual, based on the keyword included in the first user query being not searched in the counseling manual, acquire the answer by searching for the keyword included in the first user query in the plurality of counseling histories, and based on the keyword included in the first user query being not searched in the plurality of counseling histories, acquire the answer by searching for the keyword included in the first user query from the external search engine.

The processor may be configured to update the answer by removing unnecessary sentences or contents from the answer or by summarizing sentences or contents included in the answer.

According to an embodiment of the disclosure, a method for controlling an electronic apparatus includes identifying a plurality of counseling end histories among a plurality of counseling histories, each of the plurality of counseling end histories indicating that a counseling has failed to answer a user query, based on a ratio of the plurality of counseling end histories to the plurality of counseling histories being equal to or greater than a threshold ratio, identifying a first user query based on the plurality of counseling end histories, and based on a number of second user queries having a similarity to the identified first user query being equal to or greater than a first threshold number, acquiring an answer to the first user query.

The method may further include acquiring a dialogue-type scenario with respect to the first user query based on the acquired answer; and storing the acquired scenario.

The method may further include, based on a counseling including a query having a similarity to the first user query equal to or greater than a threshold value being started, performing a counseling based on the acquired scenario.

The identifying of the plurality of counseling end histories may include identifying a plurality of counseling histories for a predetermined previous time period among the plurality of counseling histories and a plurality of counseling end histories for the predetermined previous time period, and wherein the identifying of the first user query may include identifying whether a ratio of the plurality of counseling end histories identified for the predetermined previous time period to the plurality of counseling histories identified for the predetermined previous time period are equal to or greater than the threshold ratio.

The identifying of the first user query may include identifying a plurality of keywords in user queries included in the plurality of counseling end histories; identifying a predetermined number of keywords based on a number of each of the plurality of keywords; and based on the number of each of the identified keywords being equal to or greater than a second threshold number, identifying, as the first user query, a user query included in a history including the most identified keywords among the plurality of counseling end histories.

The acquiring of the answer to the first user query may include acquiring the answer by searching for a keyword included in the first user query in at least one of a counseling manual, the plurality of counseling histories, and an external search engine.

The acquiring of the answer to the first user query may include, based on the keyword included in the first user query being not searched in the counseling manual, additionally identifying a keyword in a counseling end history including the first user query, and acquiring the answer by searching for the additionally identified keyword in the counseling manual.

Based on counseling histories including the keyword included in the first user query being searched among the plurality of counseling histories, the answer may be acquired based on a relatively short counseling history among the searched counseling histories.

The acquiring of the answer by searching for the keyword included in the first user query may include acquiring the answer by searching for the keyword included in the first user query in the counseling manual, based on the keyword included in the first user query being not searched in the counseling manual, acquiring the answer by searching for the keyword included in the first user query in the plurality of counseling histories, and based on the keyword included in the first user query being not searched in the plurality of counseling histories, acquiring the answer by searching for the keyword included in the first user query from the external search engine.

According to an embodiment of the disclosure, there is provided a non-transitory computer-readable recording medium having recorded thereon a program for executing the method for controlling the electronic apparatus.

According to various embodiments of the disclosure as described above, the electronic apparatus may identify a user query for which a counseling has ended with a failure to answer, acquire an answer to the identified user query, and enhance conversational skills with the user by automatically changing the acquired answer to a dialogue-type scenario.

In addition, since the electronic apparatus may enable to answer a user query even before an administrator generates a new scenario, thereby increasing user convenience.

BRIEF DESCRIPTION OF THE DRAWINGS

FIG. 2 is a block diagram illustrating a software configuration of an electronic apparatus according to an embodiment;

FIG. 3 is a block diagram illustrating a detailed configuration of an electronic apparatus according to an embodiment;

FIG. 5 is a view illustrating a log analysis module according to an embodiment;

FIG. 6 is a view illustrating a first user query identification module according to an embodiment;

FIG. 9 is a view illustrating a scenario generation module according to an embodiment;

FIG. 10 is a view illustrating a chatbot learning according to an embodiment.

DETAILED DESCRIPTION

Figure 1:
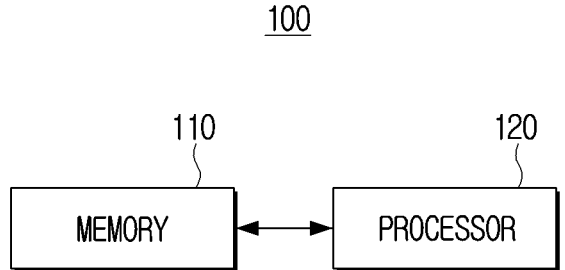
FIG. 1 is a block diagram illustrating a hardware configuration of an electronic apparatus according to an embodiment.

The example embodiments of the present disclosure may be diversely modified. Accordingly, specific example embodiments are illustrated in the drawings and are described in detail in the detailed description. However, it is to be understood that the present disclosure is not limited to a specific example embodiment, but includes all modifications, equivalents, and substitutions without departing from the scope and spirit of the present disclosure. Also, well-known functions or constructions are not described in detail since they would obscure the disclosure with unnecessary detail.

Hereinafter, the disclosure will be described in detail with reference to the accompanying drawings.

Terms used in the disclosure are selected as general terminologies currently widely used in consideration of configurations and functions of the one or more embodiments of the disclosure, but can be different depending on intention of those skilled in the art, a precedent, appearance of new technologies, or the like. Further, in specific cases, terms may be arbitrarily selected. In that configuration, the meaning of the terms will be described in the description of the corresponding embodiments. Accordingly, the terms used in the description should not necessarily be construed as simple names of the terms, but be defined based on meanings of the terms and overall contents of the disclosure.

The terms "have", "may have", "include", and "may include" used in the example embodiments of the disclosure indicate the presence of corresponding features (for example, elements such as numerical values, functions, operations, or parts), and do not preclude the presence of additional features.

The term "at least one of A or/and B" means including at least one A, including at least one B, or including both at least one A and at least one B.

The term such as "first" and "second" used in various example embodiments may modify various elements regardless of an order and/or importance of the corresponding elements, and does not limit the corresponding elements.

Singular forms are intended to include plural forms unless the context clearly indicates otherwise. The terms "include", "comprise", "is configured to," etc., of the description are used to indicate that there are features, numbers, steps, operations, elements, parts or combination thereof, and they should not exclude the possibilities of combination or addition of one or more features, numbers, steps, operations, elements, parts or a combination thereof.

Also, the term "user" may refer to a person who uses an electronic apparatus or an apparatus (e.g., an artificial intelligence (AI) electronic apparatus) that uses the electronic apparatus.

Hereinafter, embodiments will be described in greater detail with reference to the accompanying drawings.

FIG. 1 is a block diagram illustrating a hardware configuration of an electronic apparatus according to an embodiment.

The electronic apparatus 100 is an apparatus that generates an answer to the user query, and may be implemented as a server, a computer body, a desktop PC, a TV, a notebook computer, a smartphone, a tablet PC, a set-top box (STB), or the like.

However, the disclosure is not limited thereto, and the electronic apparatus 100 may be any device capable of generating an answer to the user query.

Referring to FIG. 1, the electronic apparatus 100 includes a memory 110 and a processor 120. However, the disclosure is not limited thereto, and the electronic apparatus 100 may be implemented in a form in which some components are excluded.

At least one instruction or module required for the operation of the electronic apparatus 100 or the processor 120 may be stored in the memory 110. The instruction is a unit of code indicating the operation of the electronic apparatus 100 or the processor 120, and may be provided in machine language, which is a language understandable by a computer. The module may be a set of instructions that perform a specific task in a unit of work.

The memory 110 may store data, which is information in units of bits or bytes capable of representing texts, numbers, images, or the like. For example, the memory 110 may store a plurality of counseling histories including answers to the user queries. Here, each of the plurality of counseling histories may include information on a counseling target, a counseling time, a question content, an answer, or the like. In addition, the plurality of counseling histories may include a plurality of counseling end histories each indicating that a counseling has failed to answer a user queries.

In addition, at least one artificial intelligence model for processing a user voice signal may be stored in the memory 110. Here, the artificial intelligence model may include a plurality of neural network layers and each layer of the plurality of neural network layers may include a plurality of weight values, and a computation of the layer may be performed through a calculation result of a previous layer and the plurality of weight values. Examples of neural networks include convolutional neural network (CNN), deep neural network (DNN), recurrent neural network (RNN), restricted Boltzmann machine (RBM), deep belief network (DBN), bidirectional recurrent deep neural network (BRDNN) and deep Q-networks, and the neural network in the disclosure is not limited to the examples described above, except as otherwise specified. In addition, the artificial intelligence model may be composed of an ontology-based data structure in which various concepts, conditions, relationships, or agreed knowledge are expressed in a form that can be processed by a computer.

The artificial intelligence model may be learned through the electronic apparatus 100 or a separate server/system through various learning algorithms. The learning algorithm is a method in which a predetermined target device (e.g., a robot) is trained using a plurality of learning data such that the predetermined target device can make a decision or make a prediction by itself. Examples of learning algorithms may include supervised learning, unsupervised learning, semi-supervised learning, or reinforcement learning, and different learning algorithms may be used.

The memory 110 may be accessed by the processor 120, and may include an instruction, a module, an artificial intelligence model, or data for which readout, recording, correction, deletion, update, and the like is performed by the processor 120.

The processor 120 controls a general operation of the electronic apparatus 100. Specifically, the processor 120 may be connected to components of the electronic apparatus 100 to control the components of the electronic apparatus 100. For example, the processor 120 may be connected to components such as the memory 100, a display (not shown), a communication interface (not shown), and a microphone (not shown) to control the operation of the electronic apparatus 100.

According to an embodiment, the processor 120 may be implemented as a digital signal processor (DSP), a microprocessor, or a time controller (TCON). However, it is not limited thereto, and may include one or more of a central processing unit (CPU), microcontroller unit (MCU), micro processing unit (MPU), controller, application processor (AP), or communication processor (CP), ARM processor, or may be defined with a corresponding term. In addition, the processor 120 may be implemented as a system on chip (SoC), a large scale integration (LSI) with a built-in processing algorithm, or a field programmable gate array (FPGA).

The processor 120 may identify a plurality of counseling end histories each indicating that a counseling has failed to answer a user query from among the plurality of counseling histories stored in the memory 110, and when a ratio of the plurality of counseling end histories to the plurality of counseling histories is equal to or greater than a threshold ratio, a first user query may be identified based on the plurality of counseling end histories, and when a number of second user queries having a similarity to the identified first user query is equal to or greater than a threshold number, an answer to the first user query may be acquired.

The operation of the processor 120 will be described in more detail through various modules of FIG. 2.

FIG. 2 is a block diagram illustrating a software configuration of the electronic apparatus 100 according to an embodiment. In FIG. 2, the plurality of modules are located inside the processor 120 may indicate a state in which the plurality of modules are loaded (or executed) by the processor 120 and operated in the processor 120, and the plurality of modules may be in a state previously stored in the memory 110.

Referring to FIG. 2, a plurality of counseling histories and scenarios for each situation may be stored in the memory 110. For example, when a user query is received, the electronic apparatus 100 may provide an answer to the user query based on a scenario for each situation. When the counseling with the user is finished, the electronic apparatus 100 may store the counseling history in the memory 110.

In addition, the processor 120 may control the overall operation of the electronic apparatus 100 by executing a module or an instruction stored in the memory 110. Specifically, the processor 120 may determine a sequence for data processing by reading and interpreting the module or the instruction, and accordingly control an operation of the other configuration by transmitting a control signal that controls the operation of the other configuration, such as the memory 110, or the like.

The processor 120 may identify a plurality of counseling end histories among the plurality of counseling histories stored in the memory 110 by executing an answer generation determination module. For example, the processor 120 may identify the plurality of counseling end histories among the plurality of counseling histories stored in the memory 110 at predetermined time intervals. Alternatively, the processor 120 may identify a plurality of counseling end histories among the plurality of counseling histories stored in the memory 110 at a predetermined time point, for example, 3:00 a.m.

However, the disclosure is not limited thereto, and the processor 120 may identify the counseling history in real time, count the counseling end history in the same type when the counseling fails to answer, and perform the following answer generation operation when the number of failures exceeds a threshold number.

The processor 120 may identify whether a ratio of the plurality of counseling end histories to the plurality of counseling histories is equal to or greater than a threshold ratio. For example, the processor 120 may identify a plurality of counseling histories for a predetermined previous time period and a plurality of counseling end histories each indicating that a counseling has failed to answer a user query, among the plurality of counseling histories, based on a current time point, and identify whether a ratio of the plurality of counseling end histories identified during the predetermined previous time period to the plurality of counseling histories identified during the predetermined previous time period is greater than or equal to the threshold ratio. For example, the processor 120 may identify 50 cases of a plurality of counseling histories for 2 hours based on the current time point and 20 cases of a plurality of counseling end histories for 2 hours based on the current time point, and identify whether the ratio, that is 40%, is greater than or equal to 30% of the threshold ratio.

When the ratio of the plurality of counseling end histories to the plurality of counseling histories is equal to or greater than the threshold ratio, the processor 120 may identify the first user query based on the plurality of counseling end histories. In the above-described example, the processor 120 may identify the first user query based on the plurality of counseling end histories since the ratio of the counseling end histories to the entire counseling histories is 40% and the threshold ratio is 30% or more.

The processor 120 may identify a plurality of keywords from user queries included in the plurality of counseling end histories, identify a predetermined number of keywords based on the number of each of the plurality of keywords, and identify a user query included in a history including the highest identified keywords among the plurality of counseling end histories as the first user query when the number of each of the identified keywords is equal to or greater than a second threshold number.

For example, the processor 120 may identify keywords such as "system", "update", "phone", "earphone", "charge", or the like from the user queries included in the plurality of counseling end histories, and count the number of each of the keywords may. The processor 120 may sort each of the keywords in the order of the highest number, identify "system", "update", and "phone" in the order of the highest number, and identify whether each number of "system", "update", and "phone" is equal to or greater than the second threshold number. For example, when the number of each of "system", "update" and "phone" is 10 or more, the processor 120 may identify a user query such as "the phone does not work after system update" which includes "system", "update", and "phone" the most as the first user query.

The processor 120 may acquire an answer to the first user query when the number of second user queries having a similarity with the first user query, identified by executing the answer generation module, that is greater than or equal to the threshold value is equal to or greater than the first threshold number. For example, the processor 120 may identify a similarity between the first user query and the second user queries through an artificial intelligence model. Alternatively, the processor 120 may identify a similarity by comparing keywords of the first user query and the second user queries.

The processor 120 may acquire an answer to the first user query when the number of second user queries having a similarity with the first user query that is greater than or equal to the threshold value is equal to or greater than the first threshold number, and may not acquire the answer to the first user query when the number of second user queries having a similarity with the first user query that is greater than or equal to the threshold value is less than the first threshold number.

The processor 120 may acquire an answer by searching for a keyword included in the first user query in at least one of a counselor counseling manual, a plurality of counseling histories, or an external search engine.

For example, the processor 120 may acquire an answer by searching for the keyword included in the first user query in the counseling manual, and when the keyword included in the first user query is not found in the counseling manual, the processor 120 may acquire an answer by searching for the keyword included in the first user query in a plurality of counseling histories, and when the keyword included in the first user query is not found in the plurality of counseling histories, the processor 120 may acquire an answer by searching for the keyword included in the first user query in the external search engine.

When the keyword included in the first user query is not searched in the counseling manual, the processor 130 may additionally identify a keyword from the counseling end history including the first user query, and acquire an answer by searching for the additionally identified keyword in the counseling manual.

For example, when "system", "update", and "phone" included in the first user query such as "the phone does not work after system update" are not searched in the counseling manual, the processor 120 may additionally identify a keyword from the counseling end history including the first user query. For example, after the first user query such as "the phone does not work after system update", there may be additional user utterances such as "the screen does not turn on", and the processor 120 may acquire an answer by further searching the "screen" in the counseling manual.

When counseling histories including keywords included in the first user query are searched for from the plurality of counseling histories, the processor 120 may acquire an answer based on a relatively short counseling history among the searched counseling histories. All of the counseling histories may provide the same answer, but since there may be unnecessary conversations with the user during the counseling process, it is more efficient to acquire an answer from the relatively short counseling history among the searched counseling histories.

The processor 120 may update the answer by removing unnecessary sentences or contents from the answer or by summarizing sentences or contents included in the answer. For example, the processor 120 may remove a paragraph that does not include a search keyword from the answer, remove a paragraph that does not include a web page from the answer, or remove a paragraph that does not include an image, a video tag, or the like from the answer.

The processor 120 may acquire a dialogue-type scenario for the first user query based on the answer acquired by executing a scenario generation module, and store the acquired scenario in the memory 110. For example, the processor 120 may acquire an answer such as "Try deactivating XX setting" for an answer to the first user inquiry such as "the phone does not work after system update." In that configuration, when a user query such as "The phone does not work after system update" is input, the processor 120 may provide an answer such as "Try deactivating XX setting", and acquire a scenario such as providing a question "Has the problem been solved?" when there is no answer from the user, and store it in the memory 110 as a scenario for each situation.

When a counseling including a query having a similarity with the first user query equal to or greater than a threshold value is started, the processor 120 may perform a counseling based on the acquired scenario.

Figure 3:
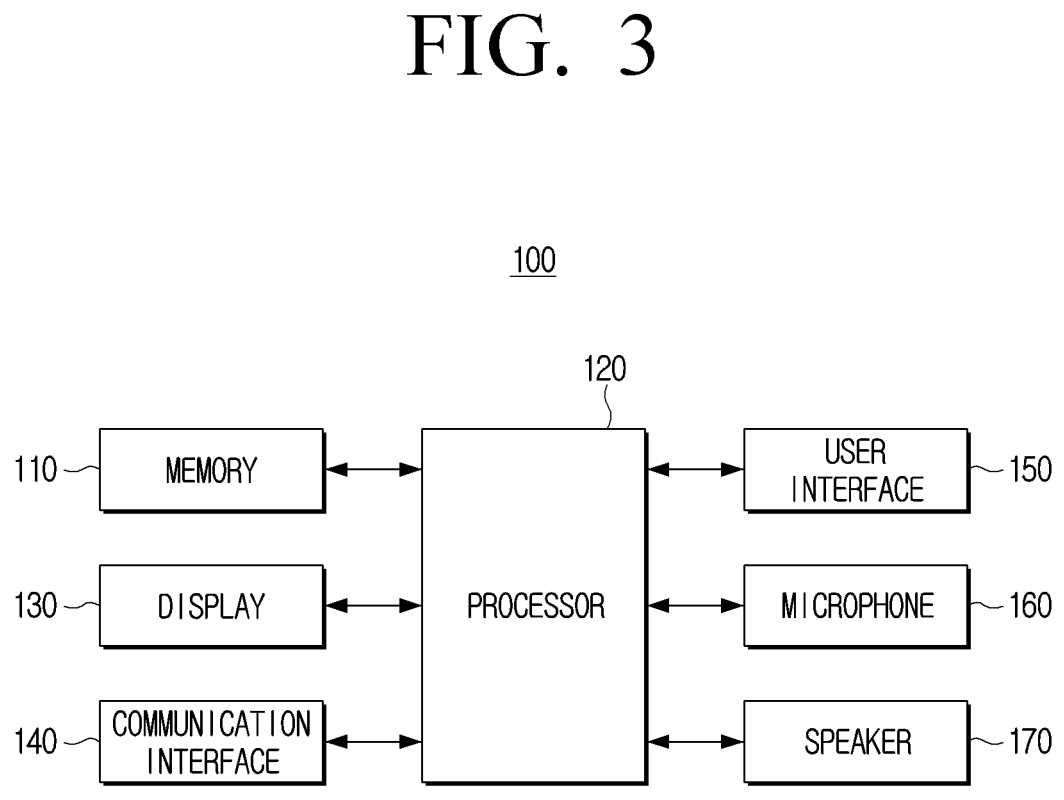

FIG. 3 is a block diagram illustrating a detailed configuration of the electronic apparatus 100 according to an embodiment. The electronic apparatus 100 may include the memory 110 and the processor 120. In addition, according to FIG. 3, the electronic apparatus 100 may further include a display 130, a communication interface 140, a user interface 150, a microphone 160, and a speaker 170. Detailed descriptions of constitutional elements illustrated in FIG. 3 that are redundant with constitutional elements in FIGS. 1 and 2 are omitted.

The display 130 may be implemented as various types of displays, such as a Liquid Crystal Display (LCD), an Organic Light Emitting Diodes (OLED) display, and a Plasma Display Panel (PDP). In the display 130, a driving circuit, a backlight unit, or the like, which may be implemented in the form of an a-si TFT, a low temperature poly silicon (LTPS) TFT, an organic TFT (OTFT), or the like may also be included. The display 130 may be realized as a touch screen, a flexible display, a 3-dimensional (3D) display, or the like.

The communication interface 140 is a component that communicates with various types of external devices according to various types of communication methods. For example, the electronic apparatus 100 may communicate with the server through the communication interface 140.

The communication interface 140 may include a Wi-Fi module, a Bluetooth module, an infrared communication module, a wireless communication module, or the like. Each communication module may be implemented in the form of at least one hardware chip.

Especially, the Wi-Fi chip and the Bluetooth chip each perform communication in the Wi-Fi method, and the Bluetooth method, respectively. If the Wi-Fi module or the Bluetooth module is used, various kinds of connection information such as a service set identifier (SSID), a session key and the like, is transmitted and received first, and after establishing communication, various kinds of information may be transmitted and received. The infrared communication module performs communication according to an infrared data association (IrDA) technology, which wirelessly transmits data in a short distance using infrared rays between sight rays and millimeter waves.

In addition to the communication methods described above, the wireless communication module may include at least one communication chip that performs communication according to various wireless communication standards such as ZigBee, 3rd generation (3G), 3rd generation partnership project (3GPP), long term evolution (LTE), LTE Advanced (LTE-A), 4th generation (4G), 5th generation (5G), and the like.

Alternatively, the communication interface 140 may include a wired communication interface such as HDMI, DP, Thunderbolt, USB, RGB, D-SUB, DVI, or the like.

In addition, the communication interface 140 may include at least one of a local area Network (LAN) module, an Ethernet module, or a wired communication module for performing communication using a pair cable, a coaxial cable, an optical fiber cable, or the like.

The user interface 150 may be implemented as a button, a touch pad, a mouse, a keyboard, or the like, or may be implemented as a touch screen capable of performing the above-described display function and manipulation input function. The button may include various types of buttons, such as a mechanical button, a touch pad, a wheel, etc., which are formed on the front, side, or rear of the exterior of a main body.

The microphone 160 is configured to receive sound and convert it into an audio signal. The microphone 160 is electrically connected to the processor 120 and may receive sound under the control of the processor 120. The sound may include sound generated by at least one of the electronic apparatus 100 and the other electronic apparatuses around the electronic apparatus 100 and noise around the electronic apparatus 100.

For example, the microphone 160 may be formed integrally with an upper side, a front direction, a side direction, or the like of the electronic apparatus 100. Alternatively, the microphone 160 may be provided in a remote control or the like separate from the electronic apparatus 100. In that configuration, the remote control may receive sound through the microphone 160 and provide the received sound to the electronic apparatus 100.

The microphone 160 may include various configurations such as a microphone that collects analog sound input, an amplifier circuit that amplifies the collected sound input, an A/D conversion circuit that samples the amplified sound input and converts the sound input into a digital signal, a filter circuit for removing noise components from the converted digital signal, or the like.

Meanwhile, the microphone 160 may be implemented in a form of a sound sensor, and any method may be used as long as it can collect sound.

The speaker 170 may be a component that outputs various types of audio data processed by the processor 120 as well as various notification sounds, voice messages, or the like.

Through the above operation, the electronic apparatus 100 may automatically generate an answer scenario with respect to a new type of user query, and may provide an answer to the user even before the administrator manually generates an answer scenario.

Hereinafter, the operation of the electronic apparatus 100 will be described in more detail with reference to FIGS. 4 to 10. Particularly, the electronic apparatus 100 is described with a chatbot. Meanwhile, individual embodiments will be described for convenience of description with reference to FIGS. 4 to 10. However, the individual embodiments of FIGS. 4 to 10 may be embodied in any combination.

Figure 4:
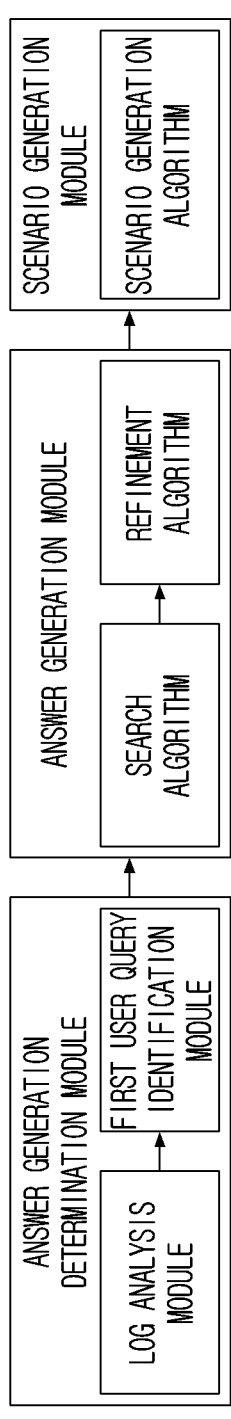
FIG. 4 is a view schematically illustrating a method of acquiring an answer to a user query according to an embodiment.

FIG. 4 is a view schematically illustrating a method of acquiring an answer to a user query according to an embodiment.

The processor 120 may identify the first user query requiring answer generation by executing the answer generation determination module. The answer generation determination module may include a log analysis module and a first user query identification module.

For example, the processor 120 may identify a plurality of counseling end histories each indicating a recent failure of a counseling to answer a user query by executing the log analysis module. For example, the processor 120 may identify a plurality of counseling end histories among the plurality of counseling histories, and identify that a new issue has been occurred when a ratio of the plurality of counseling end histories to the plurality of counseling histories is greater than or equal to a threshold ratio. In that configuration, the processor 120 may perform an operation for identifying the first user query corresponding to the new issue by executing the first user query identification module.

The processor 120 may acquire an answer to the first user query by executing the answer generation module. The answer generation module may include a search algorithm and a refinement algorithm.

For example, the processor 120 may search for a keyword included in the first user query according to the search algorithm. In addition, when an answer corresponding to the first user query is acquired, the processor 120 may update the answer by removing unnecessary sentences or contents from the answer or by summarizing sentences or contents included in the answer according to the refinement algorithm.

The processor 120 may generate a scenario corresponding to the answer by executing the scenario generation module. The scenario generation module may include a scenario generation algorithm.

For example, the processor 120 may acquire a dialogue-type scenario with respect to the first user query based on the answer.

FIG. 5 is a view illustrating a log analysis module according to an embodiment.

The processor 120 may search for a counseling history input during a set time period among a plurality of counseling histories between a customer and the chatbot stored in counseling history database by executing the log analysis module (S510). In addition, the processor 120 may detect histories of when the chatbot failed to classify user queries once or continuously (S520).

For example, the processor 120 may identify a plurality of counseling histories from a time point 24 hours before to a current time point and a plurality of counseling end histories from the time point before 24 hours to the current time among the plurality of counseling histories. For example, when a query is received from a customer, such as "My phone does not work after system update," and an answer such as "Sorry, I did not understand your question. Could you please input that again?", the processor 120 may identify that as a counseling end history indicating that the chatbot has failed to answer a user query. However, the disclosure is not limited thereto, and there may be any number of types of counseling end histories each indicating that the chatbot has failed to answer, and there may be various time intervals for identifying the counseling end histories.

When the predetermined time point comes, the processor 120 may identify a plurality of counseling end histories that have failed to answer. For example, the processor 120 may identify a plurality of counseling end histories that have failed to answer at 3 a.m. for example when a frequency of receiving user queries becomes low.

Alternatively, the processor 120 may count counseling end histories in real time. For example, when receiving a user query and failing to answer, the processor 120 may count it immediately, and perform an answer generation operation, which will be described below, and may be performed when the counted number is equal to or greater than a threshold number. The processor 120 may not simply count cases that have failed to answer, but may classify cases that have failed to answer into a plurality of types and count for each type.

The processor 120 may identify a ratio of the counseling end histories to the searched counseling histories (S530). For example, the processor 120 may identify whether the ratio of the plurality of counseling end histories identified for the predetermined previous time period to the plurality of counseling histories identified for the predetermined previous time period is equal to or greater than a threshold ratio. For example, the processor 120 may identify the ratio of the plurality of counseling end histories from the time point 24 hours before to the current time point to the plurality of counseling histories from the time point 24 hours before to the current time point among the plurality of counseling histories, and perform the answer generation operation when the identified ratio is 50% or more.

FIG. 6 is a view illustrating a first user query identification module according to an embodiment.

As described above, when the identified ratio is equal to or greater than the threshold ratio, the processor 120 may perform an answer generation operation.

The processor 120 may extract a question input by a customer from each counseling history of the plurality of counseling histories (S610). The processor 120 may extract a token (e.g., keyword) for each query (S615). For example, the electronic apparatus 100 may include a natural language understanding processing (NLP) engine, and the NLP engine may include at least one of an NLP Tokenizer, a pre-trained language model, a similar token search, and a spell corrector. The processor 120 may extract a token from each query using the NLP Tokenizer. For example, the processor 120 may extract "system", "update", and "phone" from a query such as "The phone does not work after the system update", and may also extract tokens from the remaining queries.

The processor 120 may measure the number of tokens with respect to all the extracted tokens (S620). The processor 120 may identify token candidates among the extracted tokens. In the above example, the processor 120 may measure the number of extracted "system", the number of extracted "update", the number of extracted "phone", and measure the number of tokens extracted from the remaining queries.

The processor 120 may identify whether the number of each of the token candidates is higher than a threshold number (S625). For example, the processor 120 may sort each token of the extracted tokens in the order of the largest number, for example, identify three tokens with a large number, and then identify whether the measured number of each of the three tokens is higher than the threshold number. The processor 120 may not proceed with the answer generation operation when the measured number of each of the three large tokens is lower than the threshold number.

The processor 120 may extract an embedding of the query including the most number of token candidates (S630). An operation of extracting the embedding may refer to expressing a word or sentence as a vector. The processor 120 may measure a similarity between embedding of queries including all or the most number of token candidates and embedding of other queries (S635). For example, the processor 120 may express a query including the most number of token candidates as a vector by using the pre-trained language model and similar token search, and measure the similarity between the queries expressed as the vector.

The processor 120 may identify the number of queries with a high similarity to the corresponding query (S640), stop the answer generation operation when the number is less than the threshold value (S650), and correct typos and grammar of the corresponding query when the number is greater than or equal to the threshold value (S645). In that configuration, the processor 120 may correct typos and grammar of the corresponding question by using the spell corrector, and may perform the operation of generating an answer to the corrected query (S655).

Figure 7:
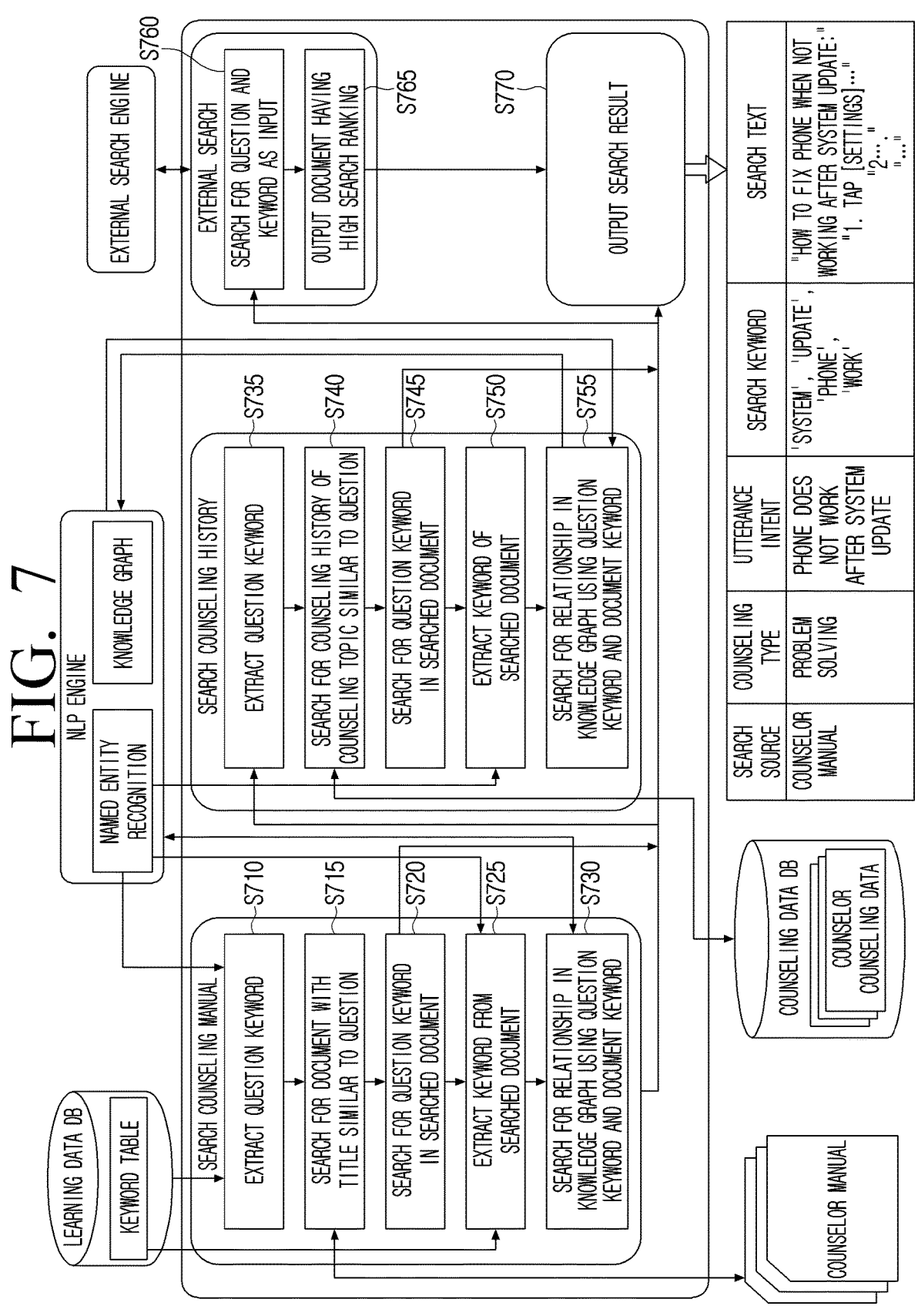
FIG. 7 is a view illustrating a search algorithm according to an embodiment.

FIG. 7 is a view illustrating a search algorithm according to an embodiment.

The processor 120 may search a counseling manual to generate an answer to a user query. The processor 120 may extract a question keyword from a user query (S710). For example, the processor 120 may extract a question keyword from the user query by using a keyword table stored in the learning data database. For example, the processor 120 may extract "system", "update", "phone", and "operation" as keywords from a user query such as "The phone does not work after the system update." Alternatively, the processor 120 may extract a question keyword from the user query using the named entity recognition of a NLP engine.

The processor 120 may search for a document with a title similar to the question (S715), and search for the question keyword in the searched document (S720). The processor 120 may extract a keyword from the searched document (S725), search for a relationship in a knowledge graph using the question keyword and the document keyword (S730), and output a search result (S770). The knowledge graph may refer to a method of combining a question-specific entity name and keywords, and a document-specific entity name and keywords in an ordered pair, and search for paths as a start node and a relational edge, and deciding to use the corresponding document when the searched final node overlaps or there is a path that most of the searched paths overlap. The processor 120 may search for a relationship in the knowledge graph using the named entity recognition of the NLP engine.

When a document unique entity name of the same type as a question unique entity name exists and entity names are different from each other, the processor 120 may output a result of replacing the corresponding entity name with the question entity name in the document. For example, the processor 120 may derive an answer such as "Try turning the power off and on for the battery problem of S10" from the counseling manual stating, "Try turning the power off and on for the battery problem of S9".

When none of the keywords are matched in the searched document, the processor 120 may further extract a keyword of the document and analyze a path of a counseling domain knowledge graph together with a question keyword.

When an answer is not acquired through the counseling manual search, the processor 120 may search counseling history. The processor 120 may extract a question keyword (S735) and search for a counseling history of a counseling topic similar to the question (S740). The processor 120 may search for the question keyword in the searched document (S745), extract a keyword of the searched document (S750), and search for a relationship in the knowledge graph using the question keyword and the document keyword (S755).

When a plurality of counseling histories are searched, the processor 120 may acquire an answer based on a relatively short counseling history among the searched counseling histories. This is because there may be unnecessary conversations between the counselor and the user in the counseling history.

When an answer is not acquired through the counseling history search, the processor 120 may use an external search engine. The processor 120 may search for a question and a keyword as input (S760), and output a document having a high search ranking (S765).

Through the above operation, the processor 120 may acquire an answer to the user query.

Figure 8:
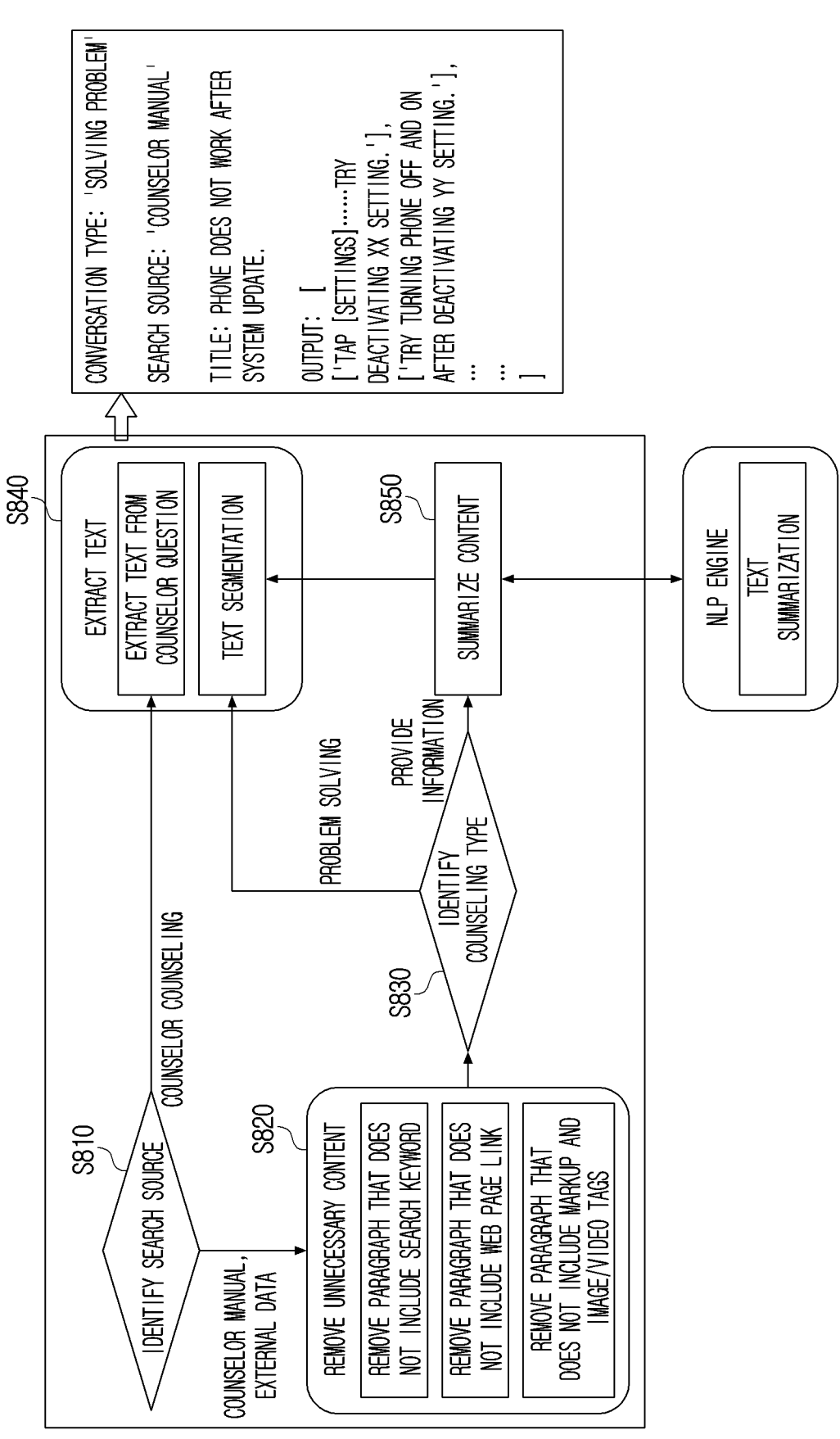
FIG. 8 is a view illustrating a refinement algorithm according to an embodiment.

FIG. 8 is a view illustrating a refinement algorithm according to an embodiment.

The processor 120 may identify a search source (S810). When the search source is a counselor manual or an external source, the processor 120 may remove unnecessary content (S820). For example, when the search source is a counselor manual or an external source, the processor 120 may remove a paragraph that does not include a search keyword, remove a paragraph that does not include a web page link, or remove a paragraph that does not include markup and image/video tags.

Thereafter, the processor 120 may identify a counseling type (S830) and summarize the content when information is provided (S850). For example, the processor 120 may summarize the content using text summarization of the NLP engine. The processor 120 may classify a paragraph of the summarized content (text segmentation, S840).

Alternatively, when the counseling type is problem solving, the processor 120 may classify a paragraph of content from which unnecessary content is removed without summarizing the content (S840).

Meanwhile, when the search source is counselor counseling, the processor 120 may extract the text (S840).

Through the above operation, the processor 120 may refine the answer. However, the disclosure is not limited thereto, and the processor 120 may refine the answer through an artificial intelligence model.

FIG. 9 is a view illustrating a scenario generation module according to an embodiment.

The left side of FIG. 9 shows a refined result after a search. The processor 120 may change the refined content into a dialogue-type scenario.

The processor 120 may extract conversation data by outputting a chatbot answer and an identification query sentence and outputting a customer answer option. In addition, the processor 120 may generate a scenario through generating conversation step-by-step and branching next steps and sequence processing.

For example, when a user query such as "The phone does not work after the system update" is received, the processor 120 may provide an answer such as "Is it correct that the subject you want to inquire is 'The phone does not work after the system update'?", and generate answers in case the customer answer is yes or no. When the customer answer is yes, the processor 120 may provide an answer such as "Press [Settings] . . . try deactivating setting xx", and when the customer answer is no, the processor 120 may provide an answer such as "Please ask again."

The processor 120 may provide an answer such as "Press [Settings] . . . try deactivating xx setting", and then provide an answer such as "Has the problem been solved?", and when the customer answer is yes, the processor 120 may end, and when the customer answer is no, the processor 120 may provide a next step answer, such as "Deactivate yy settings and turn on the phone again."

The processor 120 may change the answer into a dialogue-type scenario in the manner described above.

FIG. 10 is a view illustrating chatbot learning according to an embodiment.

The processor 120 may acquire similar sentences from a user query using a question paraphrase generator of the NLP engine, and store the acquired sentences and scenarios in learning data database.

The processor 120 may learn a classification trainer of the NLP engine with similar sentences and existing paraphrase data, load a newly learned model in the intent classifier when learning is completed, analyze the user query by using the newly loaded model, and provide answers.

Figure 11:
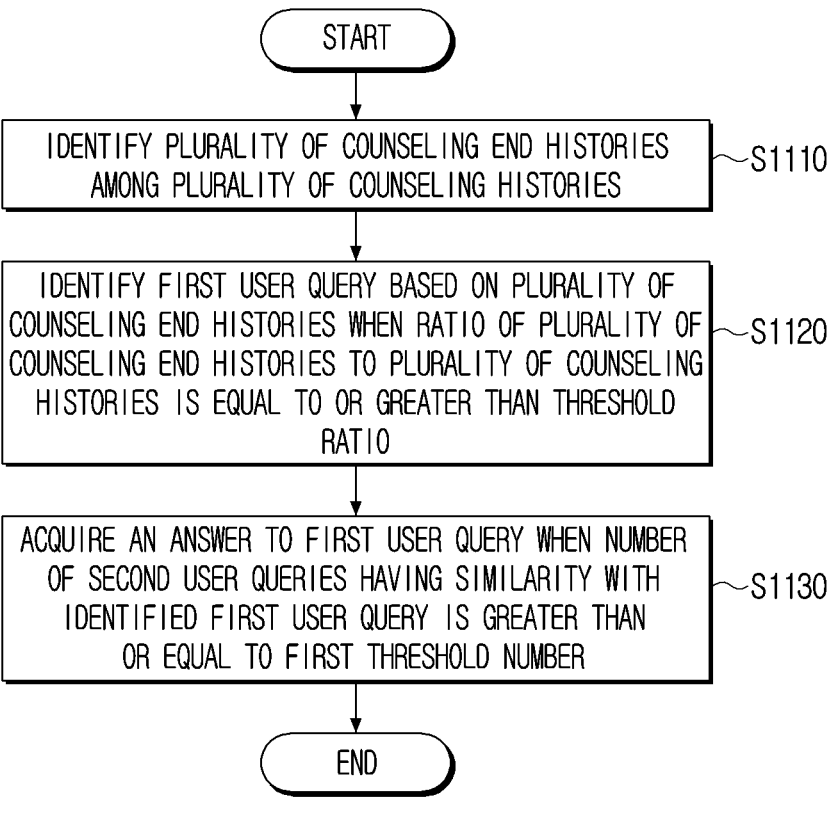
FIG. 11 is a flowchart illustrating a method of controlling an electronic apparatus according to an embodiment.

FIG. 11 is a flowchart illustrating a method of controlling an electronic apparatus according to an embodiment.

Among the plurality of counseling histories, a plurality of counseling end histories may be identified (S1110). In addition, when the ratio of the plurality of counseling end histories to the plurality of counseling histories is equal to or greater than the threshold ratio, the first user query based on the plurality of counseling end histories may be identified (S1120). In addition, an answer to the first user query may be acquired when the number of second user queries having a similarity with the identified first user query is greater than or equal to the first threshold number (S1130).

The method may further include acquiring a dialogue-type scenario for the first user query based on the acquired answer and storing the acquired scenario.

The method may further include performing a counseling based on the acquired scenario, when a counseling including a query having a similarity with the first user query equal to or greater than a threshold value is started.

Meanwhile, the identifying of the plurality of counseling histories (S1110) may include identifying the plurality of counseling histories for a predetermined previous time period based on a current time point and identifying a plurality of counseling end histories for the predetermined previous time period among the plurality of counseling histories, and the identifying the first user query (S1120) may include identifying whether a ratio of the plurality of counseling end histories identified during the predetermined previous time period to the plurality of counseling histories identified during the predetermined previous time period is greater than or equal to the threshold ratio.

In addition, the identifying of the first user query (S1120) may include identifying a plurality of keywords from the user queries included in the plurality of counseling end histories, identifying a predetermined number of keywords based on the number of each of the plurality of keywords, and identifying a user query included in a history including the highest identified keywords among a plurality of counseling end histories as the first user query when the number of each of the identified keywords is equal to or greater than a second threshold number.

The acquiring (S1130) may include acquiring an answer by searching for a keyword included in the first user query in at least one of a counseling manual, a plurality of counseling histories, or an external search engine.

When the keyword included in the first user query is not searched in the counseling manual, the acquiring (S1130) may include additionally identifying a keyword from the counseling end history including the first user query, and acquiring an answer by searching for the additionally identified keyword in the counseling manual.

When counseling histories including keywords included in the first user query are searched for from the plurality of counseling histories, the acquiring (S1130) may include acquiring an answer based on a relatively short counseling history among the searched counseling histories.

Meanwhile, the acquiring (S1130) may include acquiring an answer by searching for a keyword included in the first user query in the counseling manual, and when the keyword included in the first user query is not found in the counseling manual, the processor 120 may acquire an answer by searching for a keyword included in the first user query in a plurality of counseling histories, and when the keyword included in the first user query is not found in a plurality of counseling histories, the processor 120 may acquire an answer by searching for the keyword included in the first user query in an external search engine.

In addition, the method may further include updating the answer by removing unnecessary sentences or contents from the answer or by summarizing sentences or contents included in the answer may be further included.

According to various embodiments of the disclosure as described above, the electronic apparatus may identify a user query for which a counseling has failed to answer, acquire an answer to the identified user query, and enhance conversational skills with the user by automatically changing the acquired answer to a dialogue-type scenario.

In addition, since the electronic apparatus may enable to answer a user query even before an administrator generates a new scenario, thereby increasing user convenience.

Meanwhile, the various example embodiments described above may be implemented as an S/W program including an instruction stored on machine-readable (e.g., computer-readable) storage media. The machine is an apparatus which is capable of calling a stored instruction from the storage medium and operating according to the called instruction, and may include an electronic apparatus according to the above-described example embodiments. When the instructions are executed by a processor, the processor may directory perform functions corresponding to the instructions using other components or the functions may be performed under a control of the processor. The instructions may include code generated or executed by a compiler or an interpreter. The machine-readable storage media may be provided in a form of a non-transitory storage media. The 'non-transitory' means that the storage media does not include a signal and is tangible, but does not distinguish whether data is stored semi-permanently or temporarily in the storage media.

According to an example embodiment, the method according to the various example embodiments described above may be provided as being included in a computer program product. The computer program product may be traded between a seller and a buyer. The computer program product may be distributed online in the form of machine-readable storage media (e.g., compact disc read only memory (CD-ROM)) or through an application store (e.g., Play Store™). In a case of the online distribution, at least a portion of the computer program product may be at least temporarily stored or provisionally generated on the storage media such as a manufacturer's server, the application store's server, or a memory in a relay server.

In addition, according to an embodiment, various embodiments described above may be implemented in a recording media that may be read by a computer or a similar device to the computer by suing software, hardware, or a combination thereof. In some cases, the embodiments described herein may be implemented by the processor itself. In a software configuration, various embodiments described in the specification such as a procedure and a function may be implemented as separate software modules. The software modules may respectively perform one or more functions and operations described in the disclosure According to various embodiments described above, computer instructions for performing processing operations of a device according to the various embodiments described above may be stored in a non-transitory computer-readable medium. The computer instructions stored in the non-transitory computer-readable medium may cause a particular device to perform processing operations on the device according to the various embodiments described above when executed by the processor of the particular device. The non-transitory computer-readable medium does not refer to a medium that stores data for a short period of time, such as a register, cache, memory, etc., but semi-permanently stores data and is available of reading by the device. For example, the non-transitory computer-readable medium may be CD, DVD, a hard disc, Blu-ray disc, USB, a memory card, ROM, or the like.

The respective components (e.g., module or program) according to the various example embodiments may include a single entity or a plurality of entities, and some of the corresponding sub-components described above may be omitted, or another sub-component may be further added to the various example embodiments. Alternatively or additionally, some components (e.g., module or program) may be combined to form a single entity which performs the same or similar functions as the corresponding elements before being combined. Operations performed by a module, a program module, or other component, according to various example embodiments, may be sequential, parallel, or both, executed iteratively or heuristically, or at least some operations may be performed in a different order, omitted, or other operations may be added.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents.

What is claimed is:

1. An electronic apparatus comprising:
a memory;
a microphone; and
a processor connected to the memory and configured to control the electronic apparatus,
wherein the processor is further configured to:
identify a plurality of counseling end histories among a plurality of counseling histories stored in the memory, each of the plurality of counseling end histories indicating that a counseling has failed to answer a user query;
based on a ratio of the plurality of counseling end histories to the plurality of counseling histories being equal to or greater than a threshold ratio, identify a first user query based on the plurality of counseling end histories;
based on a number of second user queries having a similarity to the identified first user query being equal to or greater than a first threshold number, acquire an answer to the first user query by searching in the plurality of counseling histories for a keyword included in the first user query;
acquire a dialogue-type scenario with respect to the first user query based on the acquired answer to the first user query;
store the acquired dialogue-type scenario in the memory;
receive a third user query having a similarity to the first user query equal to or greater than a threshold value through the microphone; and
perform a counseling including the third user query based on the acquired dialogue-type scenario.

2. The apparatus of claim 1, wherein the processor is further configured to:
identify a plurality of counseling histories for a predetermined previous time period among the plurality of counseling histories stored in the memory and a plurality of counseling end histories for the predetermined previous time period, and
identify whether a ratio of the plurality of counseling end histories identified for the predetermined previous time period to the plurality of counseling histories identified for the predetermined previous time period are equal to or greater than the threshold ratio.

3. The apparatus of claim 1, wherein the processor is further configured to:
identify a plurality of keywords in user queries included in the plurality of counseling end histories,
identify a predetermined number of keywords based on a number of each of the plurality of keywords, and
based on the number of each of the identified keywords being equal to or greater than a second threshold number, identify, as the first user query, a user query included in a history including a most identified keywords among the plurality of counseling end histories.

4. The apparatus of claim 1, wherein the processor is further configured to acquire the answer by further searching for the keyword included in the first user query in at least one of a counseling manual and an external search engine.

5. The apparatus of claim 4, wherein the processor is further configured to:
based on the keyword included in the first user query being not searched in the counseling manual, additionally identify a keyword in a counseling end history including the first user query, and acquire the answer by searching for the additionally identified keyword in the counseling manual.

6. The apparatus of claim 4, wherein the processor is further configured to, based on counseling histories including the keyword included in the first user query being searched among the plurality of counseling histories, acquire the answer based on a relatively short counseling history among the searched counseling histories.

7. The apparatus of claim 4, wherein the processor is further configured to:

acquire the answer by searching for the keyword included in the first user query in the counseling manual, based on the keyword included in the first user query being not searched in the counseling manual, acquire the answer by searching for the keyword included in the first user query in the plurality of counseling histories, and based on the keyword included in the first user query being not searched in the plurality of counseling histories, acquire the answer by searching for the keyword included in the first user query from the external search engine.

8. The apparatus of claim 1, wherein the processor is further configured to update the answer by removing unnecessary sentences or contents from the answer or by summarizing sentences or contents included in the answer.

9. A method for controlling an electronic apparatus, the method comprising:

identifying a plurality of counseling end histories among a plurality of counseling histories, each of the plurality of counseling end histories indicating that a counseling has failed to answer a user query;

based on a ratio of the plurality of counseling end histories to the plurality of counseling histories being equal to or greater than a threshold ratio, identifying a first user query based on the plurality of counseling end histories;

based on a number of second user queries having a similarity to the identified first user query being equal to or greater than a first threshold number, acquiring an answer to the first user query by searching in the plurality of counseling histories for a keyword included in the first user query;

acquiring a dialogue-type scenario with respect to the first user query based on the acquired answer to the first user query;

storing the acquired dialogue-type scenario;

receiving a third user query having a similarity to the first user query equal to or greater than a threshold value through a microphone included in the electronic apparatus; and performing a counseling including the third user query based on the acquired dialogue-type scenario.

10. The method of claim 9, wherein the identifying of the plurality of counseling end histories comprises identifying a plurality of counseling histories for a predetermined previous time period among the plurality of counseling histories and a plurality of counseling end histories for the predetermined previous time period, and wherein the identifying of the first user query comprises identifying whether a ratio of the plurality of counseling end histories identified for the predetermined previous time period to the plurality of counseling histories identified for the predetermined previous time period are equal to or greater than the threshold ratio.

11. The method of claim 9, wherein the identifying of the first user query comprises:

identifying a plurality of keywords in user queries included in the plurality of counseling end histories;

identifying a predetermined number of keywords based on a number of each of the plurality of keywords; and based on the number of each of the identified keywords being equal to or greater than a second threshold number, identifying, as the first user query, a user query included in a history including a most identified keywords among the plurality of counseling end histories.

12. The method of claim 9, wherein the acquiring of the answer to the first user query comprises acquiring the answer by further searching for the keyword included in the first user query in at least one of a counseling manual, and an external search engine.

13. The method of claim 12, wherein the acquiring of the answer to the first user query comprises:

based on the keyword included in the first user query being not searched in the counseling manual, additionally identifying a keyword in a counseling end history including the first user query, and acquiring the answer by searching for the additionally identified keyword in the counseling manual.

14. The method of claim 12, wherein based on counseling histories including the keyword included in the first user query being searched among the plurality of counseling histories, the answer is acquired based on a relatively short counseling history among the searched counseling histories.

15. The method of claim 12, wherein the acquiring of the answer by searching for the keyword included in the first user query comprises:

acquiring the answer by searching for the keyword included in the first user query in the counseling manual, based on the keyword included in the first user query being not searched in the counseling manual, acquiring the answer by searching for the keyword included in the first user query in the plurality of counseling histories, and based on the keyword included in the first user query being not searched in the plurality of counseling histories, acquiring the answer by searching for the keyword included in the first user query from the external search engine.

16. A non-transitory computer-readable recording medium having recorded thereon a program for executing the method of claim 9.

* * * * *